US009164060B2

(12) United States Patent
Campbell et al.

(10) Patent No.: US 9,164,060 B2
(45) Date of Patent: Oct. 20, 2015

(54) REDUCING INTERFERENCES IN ISOBARIC TAG-BASED QUANTIFICATION (71) Applicant: DH Technologies Development Pte. Ltd., Singapore (SG)

(72) Inventors: John Lawrence Campbell, Milton (CA); Yves LeBlanc, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 14/401,399

(22) PCT Filed: May 17, 2013

(86) PCT No.: PCT/IB2013/000963
§ 371 (c)(1),
(2) Date: Nov. 14, 2014

(87) PCT Pub. No.: WO2013/171569
PCT Pub. Date: Nov. 21, 2013

(65) Prior Publication Data
US 2015/0129762 A1 May 14, 2015

Related U.S. Application Data (60) Provisional application No. 61/649,055, filed on May 18, 2012.

(51) Int. Cl.
H01J 49/40 (2006.01)
G01N 33/22 (2006.01)
G01N 27/62 (2006.01)
H01J 49/00 (2006.01)
H01J 49/04 (2006.01)

(52) U.S. Cl.
CPC .......... *G01N 27/624* (2013.01); *H01J 49/0031* (2013.01); *H01J 49/0431* (2013.01)

(58) Field of Classification Search
CPC .............. G01N 27/622; G01N 67/624; G01N 15/0266; G01N 33/22; H01J 49/0404; H01J 49/26; H01J 49/0031; H01J 49/04; H01J 49/0422; H01J 49/40; H01J 49/004; H01J 49/0077; H01J 49/24
USPC .......... 250/281, 282, 287, 288, 289, 290, 291, 250/424
See application file for complete search history.

(56) References Cited

U.S. PATENT DOCUMENTS 7,129,482 B2 * 10/2006 Miller et al. ................... 250/288
7,982,183 B2 * 7/2011 Makarov et al. .............. 250/283
8,030,610 B2 * 10/2011 Guo et al. ...................... 250/281
8,076,636 B2 * 12/2011 Giles ............................. 250/282

(Continued)

FOREIGN PATENT DOCUMENTS

WO 2011-100192 8/2011

OTHER PUBLICATIONS

International Search Report from International Patent Application No. PCT/IB2013/000963, dated Sep. 2, 2013.

*Primary Examiner* — David A Vanore (57) ABSTRACT

Methods and systems for performing mass spectrometry of analytes labeled with isobaric tags are provided herein. In accordance with various aspects of the applicants' teachings, the methods and systems can enable enhanced discrimination between an analyte of interest and one or more interfering species when using isobaric tagging techniques.

20 Claims, 3 Drawing Sheets

(56) References Cited

U.S. PATENT DOCUMENTS

| | | | |
|---|---|---|---|
| 8,084,736 B2* | 12/2011 | Schneider et al. | 250/289 |
| 8,410,431 B2* | 4/2013 | Ouyang et al. | 250/288 |
| 2008/0164409 A1* | 7/2008 | Schultz et al. | 250/282 |
| 2010/0282966 A1* | 11/2010 | Schneider et al. | 250/282 |
| 2011/0183431 A1* | 7/2011 | Covey et al. | 436/173 |
| 2011/0207228 A1 | 8/2011 | Sohn et al. | |
| 2011/0220790 A1* | 9/2011 | Sun et al. | 250/288 |
| 2011/0226944 A1 | 9/2011 | Holmquist et al. | |
| 2012/0056085 A1* | 3/2012 | Giles et al. | 250/282 |
| 2015/0008312 A1* | 1/2015 | Campbell et al. | 250/282 |

\* cited by examiner

REDUCING INTERFERENCES IN ISOBARIC TAG-BASED QUANTIFICATION

RELATED APPLICATIONS

This application claims the benefit of priority from U.S. Provisional Application Ser. No. 61/649,055, filed on May 18, 2012, the entire contents of which is incorporated by reference herein.

FIELD

The invention generally relates to mass spectrometry, and more particularly to methods and apparatus for reducing interference in isobaric tag-based quantifications using mass spectrometry.

INTRODUCTION

Mass spectrometry (MS) is an analytical technique for determining the elemental composition of test substances with both qualitative and quantitative applications. For example, MS can be useful for identifying unknown compounds, determining the isotopic composition of elements in a molecule, determining the structure of a particular compound by observing its fragmentation, and quantifying the amount of a particular compound in a sample.

MS analysis of complex samples (e.g., biological matrices) can sometimes result in inaccurate and/or non-specific detection as a result of interfering species contained within the sample that are not sufficiently resolved from the analyte of interest. Despite advances in MS that have enabled high-resolution mass analyzers to distinguish target species from interfering species within about 0.01 Th, it is not always feasible or possible to use a high-resolution mass analyzer or high-resolution analysis, for example, due to availability, cost, and/or experimental conditions.

While isobaric tagging techniques such as isobaric tags for relative and quantitative quantification (iTRAQ) and tandem mass tags (TMTs) provide a powerful tool in quantitative proteomics, such techniques might not lend themselves to high-resolution isolation by mass analyzers. In iTRAQ techniques, for example, an analyte of interest is labeled with a labeling reagent having a known molecular mass. The labeling reagent includes a reporter group, a balance group, and a reactive group that non-specifically binds the labeling reagent to the analyte of interest. Upon isolation and fragmentation of a labeled analyte of interest, the reporter group is cleaved (e.g., through collision induced dissociation, fragmentation) to enable quantification of the analyte of interest based on detection of the reporter group's characteristic signature. In multiplexing experiments, different isobaric labeling reagents can be mixed with various samples such that a particular analyte of each sample can be quantified in a single run of the MS based on the difference in mass of the unique reporter groups associated with each of the isobaric labeling reagents.

As noted above, sample peptides labeled with isobaric tags are typically isolated at resolutions much lower (e.g., ~1-4 Th) than those achievable by mass analyzers known in the art. Thus, for highly complex samples containing many peptides, the wide isolation window can result in the concurrent isolation of multiple interfering species having similar mass-to-charge ratios to that of the labeled analyte of interest. Because of the non-specific binding of the isobaric tags, the detected quantity of reporter ions might not reflect the true quantity of the specific analyte of interest.

Accordingly, there remains a need for methods and systems for enhanced discrimination between the analyte of interest and interfering species when using mass spectrometry isobaric tagging techniques.

SUMMARY

In accordance with one aspect, certain embodiments of the applicants' teachings relate to a method for performing mass spectrometry. According to the method, at least one sample containing or suspected of containing an analyte of interest can be reacted with a labeling reagent to generate a plurality of labeled analytes. The method can also include ionizing the plurality of labeled analytes to generate a plurality of labeled analyte ions, wherein the plurality of labeled analyte ions comprises labeled ions of the analyte of interest, if any, and labeled ions of an interfering species, the labeled ions of the interfering species being characterized by a m/z ratio substantially identical to that of the labeled ions of the analyte of interest. The labeled analyte ions can be reacted with a neutral reagent (i.e., a reagent without a net electrical charge such as a neutral molecule) to change the charge state of at least one of the labeled ions of the analyte of interest and the labeled ions of the interfering species such that a m/z ratio of the labeled ions of the analyte of interest differs from a m/z ratio of the labeled ions of the interfering species. Subsequently, the labeled ions of the analyte of interest can be isolated from the labeled ions of the interfering species based on the difference in m/z ratio, and fragmented so as to cleave a reporter group from the labeled ion of the analyte of interest. The method can also include detecting the reporter group.

In some aspects, reacting the at least one sample with a labeling reagent can comprise reacting each of two or more samples with a different isobaric labeling reagent, the method further comprising mixing the plurality of labeled analytes from the two or more samples. In a related aspect, each of the isobaric labeling reagents can comprise a reporter group with the reporter groups of each of the different isobaric labeling reagents differ in mass. Each of the reporter groups can be detected.

In some aspects, charge states of the labeled ions of the analyte of interest and the labeled ions of the interfering species can differ prior to reacting the labeled analyte ions with a neutral reagent. In various embodiments, the analyte of interest and the interfering species can be peptides.

In various aspects, methods in accordance with applicants' teachings can include transporting the labeled analyte ions through an ion mobility spectrometer prior to reacting the labeled analyte ions with the neutral reagent. The ion mobility spectrometer can be a differential mobility spectrometer, for example.

In some aspects, the method can include reacting the labeled analyte ions with the neutral reagent while transporting said labeled analyte ions through an ion mobility spectrometer. In various aspects, the labeled analyte ions are caused to react with the neutral reagent prior to transporting said labeled analyte ions through an ion mobility spectrometer. In some aspects, the method can include reacting the labeled analyte ions with the neutral reagent subsequent to transporting said labeled analyte ions through an ion mobility spectrometer.

In some aspects, detection of the reporter group can allow for the relative or absolute quantification of the analyte (e.g., peptide) of interest in the one or more samples.

In accordance with one aspect, certain embodiments of the applicants' teachings relate to a method for performing mass spectrometry. According to the method, a sample containing or suspected of containing an analyte of interest can be reacted with a labeling reagent having a reporter group to generate a plurality of labeled analytes. The method can also include ionizing the plurality of labeled analytes to generate a plurality of labeled analyte ions, wherein the plurality of labeled analyte ions comprises labeled ions of the analyte of interest, if any, at a first charge state characterized by a first m/z ratio. The labeled ions of the analyte of interest can be reacted with a neutral reagent so as to change the charge state of the labeled ions of the analyte of interest to a second charge state characterized by a second m/z ratio different from the first m/z ratio. The method can also include fragmenting the labeled ions of the analyte of interest characterized by the second m/z ratio so as to cleave the reporter group from the labeled ions of the analyte of interest. The reporter group can be detected.

In accordance with one aspect, certain embodiments of the applicants' teachings relate to a mass spectrometry system that includes a differential mobility spectrometer for receiving ions from an ion source, the differential mobility spectrometer having an internal operating pressure, electrodes, and at least one voltage source for providing DC and RF voltages to the electrodes. The system also includes a mass spectrometer sealed to, and in fluid communication with, the differential mobility spectrometer for receiving the ions from the differential mobility spectrometer. A vacuum chamber surrounding the mass spectrometer maintains the mass spectrometer at a vacuum pressure lower than the internal operating pressure of the differential mobility spectrometer such that the vacuum chamber is operable to draw a gas flow including the ions through the differential mobility spectrometer and into the vacuum chamber. A reaction chamber connects an outlet of the differential mobility spectrometer to an inlet of the mass spectrometer to define an ion path of travel therebetween, the reaction chamber being configured for reacting ions with a neutral reagent molecule prior to entry into the inlet of the mass spectrometer.

In some aspects, the operating pressure of the differential mobility spectrometer can be about atmospheric pressure. In various embodiments, the ions can be reacted with the neutral reagent ions at about atmospheric pressure. In some aspects, the reaction chamber can include a port for delivering neutral reagent molecules to the reaction chamber. The port can comprise a nozzle for delivering a liquid neutral reagent. In other aspects, the port supplies a gas into the reaction chamber, wherein the gas is configured to be bubbled through a neutral reagent supply prior to introduction into the reaction chamber. In related aspects, the gas port can be adjustable to vary a concentration of the neutral reagent molecule in the reaction chamber. In various aspects, the gas port can be adjustable to vary a gas flow rate through the differential mobility spectrometer. In various aspects, the system can include a supply of neutral reagent molecules, the supply being connected to the port.

These and other features of the applicants' teachings are set forth herein.

BRIEF DESCRIPTION OF THE DRAWINGS

The skilled person in the art will understand that the drawings, described below, are for illustration purposes only. The drawings are not intended to limit the scope of the applicants' teachings in any way.

DETAILED DESCRIPTION OF EMBODIMENTS

It will be appreciated that for clarity, the following discussion will explicate various aspects of embodiments of the applicants' teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicants' teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicants' teachings in any manner.

Methods and systems for performing mass spectrometry of analytes labeled with isobaric tags are provided herein. In accordance with various aspects of the applicants' teachings, the methods and systems can enable enhanced discrimination between an analyte of interest and one or more interfering species when using isobaric tagging techniques. In some broad aspects, the present teachings relate to utilizing reactions between neutral reagents (e.g., neutral molecules) and ionic species having substantially identical m/z ratios (e.g., ±2 Th) so as to cause sufficient change in their m/z ratios (e.g., via charge transfer reactions) such that those species can be resolved from one another via mass spectrometry (e.g., to allow for their direct or indirect quantification without interference from the other). By way of example, the m/z ratio of at least one of the target species and the interfering species may be changed such that the difference between their m/z ratios is greater than the operative resolution window of the mass analyzer, for example, at least about 2 Th.

Figure 1:
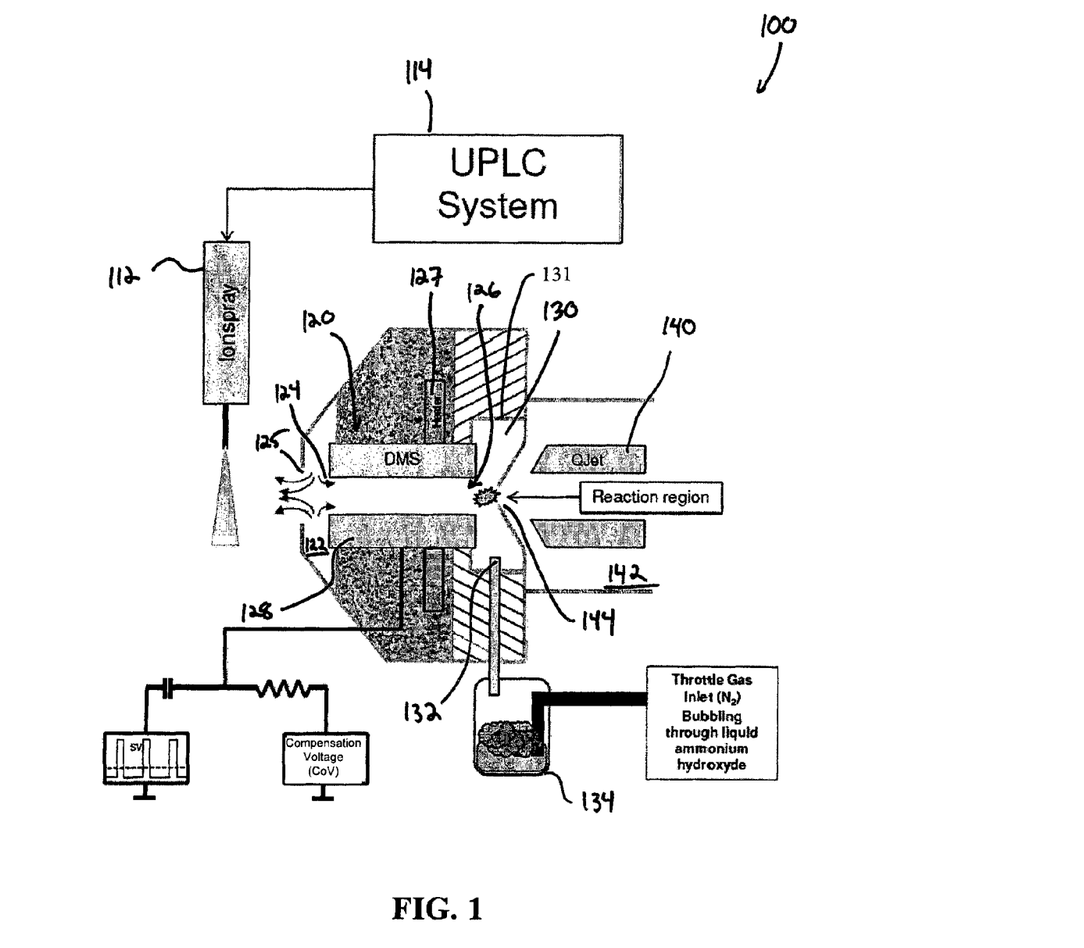
FIG. 1, in a schematic diagram, illustrates an exemplary differential mobility spectrometer/mass spectrometer system having a reaction chamber for performing ion/molecule reactions in accordance with an aspect of various embodiments of the applicants' teachings.

With reference now to FIG. 1, an exemplary mass spectrometry system 100 in accordance with various aspects of applicants' teachings is illustrated schematically. As will be appreciated by a person skilled in the art, the mass spectrometry system 100 represents only one possible configuration in accordance with various aspects of the systems, devices, and methods described herein. As shown in FIG. 1, the mass spectrometry system 100 generally includes a differential mobility spectrometer 120 in fluid communication with one or more lens elements 140 of a mass spectrometer (hereinafter generally designated mass spectrometer 140) and a reaction chamber 130 disposed between the differential mobility spectrometer 120 and the mass spectrometer 140.

Ions provided from an ion source 112 can be emitted into the curtain chamber 122 containing the differential mobility spectrometer 120 via curtain chamber orifice 125. As will be appreciated by a person skilled in the art, the ion source can be virtually any ion source known in the art, including for example, a continuous ion source, a pulsed ion source, an atmospheric pressure chemical ionization (APCI) source, an electrospray ionization (ESI) source, an inductively coupled plasma (ICP) ion source, a matrix-assisted laser desorption/ionization (MALDI) ion source, a glow discharge ion source, an electron impact ion source, a chemical ionization source, or a photoionization ion source, among others. By way of non-limiting example, as shown in FIG. 1, the sample can additionally be subjected to automated or in-line sample preparation including liquid chromatographic separation using the UPLC column 114.

The differential mobility spectrometer 120 can have a variety of configurations, but is generally configured to resolve ions received from the ion source 112 based on their mobility through a fixed or variable electric field. Though generally described herein as a differential mobility spectrometer, the mobility spectrometer 120 can utilize other techniques/systems for performing mobility spectrometry including, for example, an ion mobility spectrometer, FAIMS devices of various geometries such as parallel plate, curved electrode, or cylindrical FAIMS device, among others, and modified in light of the teachings herein.

In the exemplary embodiment depicted in FIG. 1, for example, the differential mobility spectrometer 120 can comprise opposed electrode plates 128 that surround a drift gas that drifts from an inlet 124 of the differential mobility spectrometer 120 to an outlet 126 of the differential mobility spectrometer 120. Whereas MS analyzes ions based on their mass-to-charge ratios, ion mobility spectrometry instead separates ions based on their mobility through a gas in the presence of an electric field. The drift time through the flight tube and therefore the mobility of an ion is characteristic of the size and shape of the ion and its interactions with the background gas. Differential mobility spectrometry, also referred to as high field asymmetric waveform ion mobility spectrometry (FAIMS) or Field Ion Spectrometry (FIS), applies RF voltages, referred to herein as separation voltages (SV), across the electrode plates 128 to generate an electric force in a direction perpendicular to that of the drift gas flow. Ions of a given species tend to migrate radially away from the axis of the drift tube by a characteristic amount during each cycle of the RF waveform due to differences in mobility during the high field and low field portions. A DC potential, commonly referred to as a compensation voltage (CV or CoV), is applied to the electrode plates 128 to provide a counterbalancing electrostatic force to that of the SV. The CV can be tuned so as to preferentially prevent the drift of a species of ion of interest. Depending on the application, the CV can be set to a fixed value such that only ion species exhibiting a particular differential mobility are transmitted through the outlet 126 of the differential mobility spectrometer 120 (the remaining species of ions drift toward the electrodes 128 and are neutralized thereby). As will be appreciated by a person skilled in the art, the differential mobility spectrometer 120 can also operate in "transparent" mode, for example, by setting SV to zero such that substantially all ions are transmitted therethrough without experiencing a net radial force.

As shown in FIG. 1, the differential mobility spectrometer 120 can be contained within a curtain chamber 122 that is defined by a curtain plate or boundary member 123 having an orifice 125 for receiving ions from the ion source 112. As will be appreciated by a person skilled in the art, the curtain chamber 122 can be supplied with a curtain gas from a curtain gas supply (not shown) at various flow rates, for example, as determined by a flow controller and valves. Moreover, the curtain gas supply can provide any pure or mixed composition curtain gas to the curtain gas chamber. By way of non-limiting example, the curtain gas can be air, $O_2$, He, $N_2$, $CO_2$, or any combination thereof. The pressure of the curtain gases in the curtain chamber 122 can be maintained at or near atmospheric pressure (i.e., 760 Torr). The system 100 can also include a modifier supply (not shown) for supplying a modifier agent to the curtain gas to cluster with ions differentially during the high and low field portions of the SV. By way of example, the modifier supply can be a reservoir of a solid, liquid, or gas through which the curtain gas can be delivered to the curtain chamber 122. The modifier supply can provide any modifier to the curtain gas including, by way of non-limiting example, water, methanol, acetone, isopropanol, methylene chloride, methylene bromide, or any combination thereof. In some embodiments, the curtain chamber 122 and/or the differential mobility spectrometer 120 can additionally include a heater 127 for heating the curtain gas, the modifier, and/or the drift gas to control, for example, the proportion of modifier in the curtain and/or drift gas.

The pressure of the curtain gases in the curtain chamber 122 (e.g., ~760 Torr) can provide both a curtain gas outflow out of curtain gas orifice 125, as well as a curtain gas inflow into the differential mobility spectrometer 120, which becomes the drift gas that carries the ions through the differential mobility spectrometer 120 and into a reaction chamber 130 that defines a path of travel for the ions between the differential mobility spectrometer 120 and the mass spectrometer 140 contained within the vacuum chamber 142. In some embodiments, for example, the outlet 126 of the differential mobility spectrometer 120 can be aligned with the inlet 144 of the mass spectrometer 140 to define the ion path of travel therebetween, while the walls 131 of the reaction chamber 130 are spaced from this path of travel to provide an increased reaction volume.

As shown in FIG. 1, the reaction chamber 130 can additionally comprise a port 132 through which a throttle gas and/or reagent molecules can be introduced into the reaction chamber 130. By way of example, a throttle gas comprising $N_2$ can be bubbled through a neutral reagent supply 134 containing a neutral reagent such that the throttle gas carries the neutral reagent molecules into the reaction chamber 130 for use in an ion/molecule reaction with the ions that are transmitted by the differential mobility spectrometer 120. As will be appreciated by a person skilled in the art, the flow of the throttle gas through the neutral reagent supply 134 and into the reaction chamber 130 can be controlled by a controllable valve, for example, and selected so as to throttle back (i.e., slow) the flow of the drift gas through the differential mobility spectrometer 120 and/or control the concentration of neutral reagent in the reaction chamber 130. By way of example, the flow of throttle gas into the reaction chamber 130 can be modified so as to modify the gas flow rate through the differential mobility spectrometer 120, thereby controlling the residence time of ions within the differential mobility spectrometer 120. In the embodiment of FIG. 1, for example, the inflow of throttle gas can be controlled by controlling the gas port 132. Moreover, the gas port 132 can be oriented to direct the throttle gas and/or neutral reagent throughout the reaction chamber 130, and in some embodiments, without disrupting the gas streamlines between the differential mobility spectrometer 120 and the vacuum chamber inlet 144.

A person skilled in the art will appreciate that the neutral reagent molecule can be any molecule that facilitates ion/molecule reactions such as ion-molecule adduct formation, condensation reactions, displacement/elimination reactions, clustering reactions, charge exchange reactions and proton transfer reactions, all by way of non-limiting examples.

As will be appreciated by a person skilled in the art, the vacuum chamber 142 can be maintained at a much lower pressure than the curtain chamber 122. For example, the vacuum chamber 142 can be maintained at a pressure of about 2.3 Torr by a vacuum pump (not shown), while the curtain chamber 122 and an internal operating pressure of the differential mobility spectrometer 120 can be maintained at a pressure of 760 Torr. As a result of the significant pressure differential between the curtain chamber 122 and the vacuum chamber 142, the drift gas can be drawn through the differential mobility spectrometer 120, the reaction chamber 130 and, via vacuum chamber inlet 144, into the vacuum chamber 142 and mass spectrometer 140. As shown, the mass spectrometer 140 can be sealed to (or at least partially sealed), and in fluid communication with the differential mobility spectrometer 120, via the reaction chamber 130, to receive the ions transmitted by the differential mobility spectrometer 120.

Though only mass spectrometer 140 is shown, a person skilled in the art will appreciate that the mass spectrometry system 100 can include additional mass analyzer elements downstream from the vacuum chamber 142. As such, ions transported through vacuum chamber 142 can be transported through one or more additional differentially pumped vacuum stages containing one or more mass analyzer elements. For instance, in one embodiment, a triple quadrupole mass spectrometer may comprise three differentially pumped vacuum stages, including a first stage maintained at a pressure of approximately 2.3 Torr, a second stage maintained at a pressure of approximately 6 mTorr, and a third stage maintained at a pressure of approximately $10^{-5}$ Torr. The third vacuum stage can contain, for example, a detector, as well as two quadrupole mass analyzers (e.g., Q1 and Q3) with a collision cell (Q3) located between them. It will be apparent to those skilled in the art that there may be a number of other ion optical elements in the system. This example is not meant to be limiting as it will also be apparent to those of skill in the art that the differential mobility spectrometer/mass spectrometer coupling described above can be applicable to many mass spectrometer systems that sample ions from elevated pressure sources. These can include time of flight (TOF), ion trap, quadrupole, or other mass analyzers, as known in the art.

As will be appreciated by a person skilled in the art, the vacuum chamber inlet 144 can be an orifice, or, alternatively, may be a capillary, heated capillary, or an ion pipe. In some embodiments of the present teachings, it can be advantageous to provide a braking potential (e.g., by providing a DC offset voltage to either the electrode plates 128 of the differential mobility spectrometer 120 relative to the declustering or inlet potential provided to the vacuum chamber inlet 144) to slow down the ions transmitted into the reaction chamber 130 from the differential mobility spectrometer 120. By slowing down the ions prior to entering the vacuum chamber 142, the exposure of the ions to the neutral reagent can be increased, thereby increasing the chemical reaction, and ultimately, increasing the sensitivity of detection by the mass spectrometer 140.

Though FIG. 1 depicts separate sources for the curtain gas and throttle gas containing the neutral reagent, a person skilled in the art will appreciate that systems in accord with the teachings herein can comprise a single gas source that divides into two branches that can be independently controlled to effect differences in the gas flow to the reaction chamber 130 and curtain chamber 122. It will further be appreciated that although the neutral reagent is introduced into the reaction chamber downstream of the differential mobility spectrometer 120, ion/molecule reactions can be initiated in various locations throughout the mass spectrometry system 100. By way of example, a gas port can instead be disposed upstream of the differential mobility spectrometer 120 such that the neutral reagent molecules can react with the analyte ions prior to or during their transmission through the differential mobility spectrometer 120.

Figure 2:
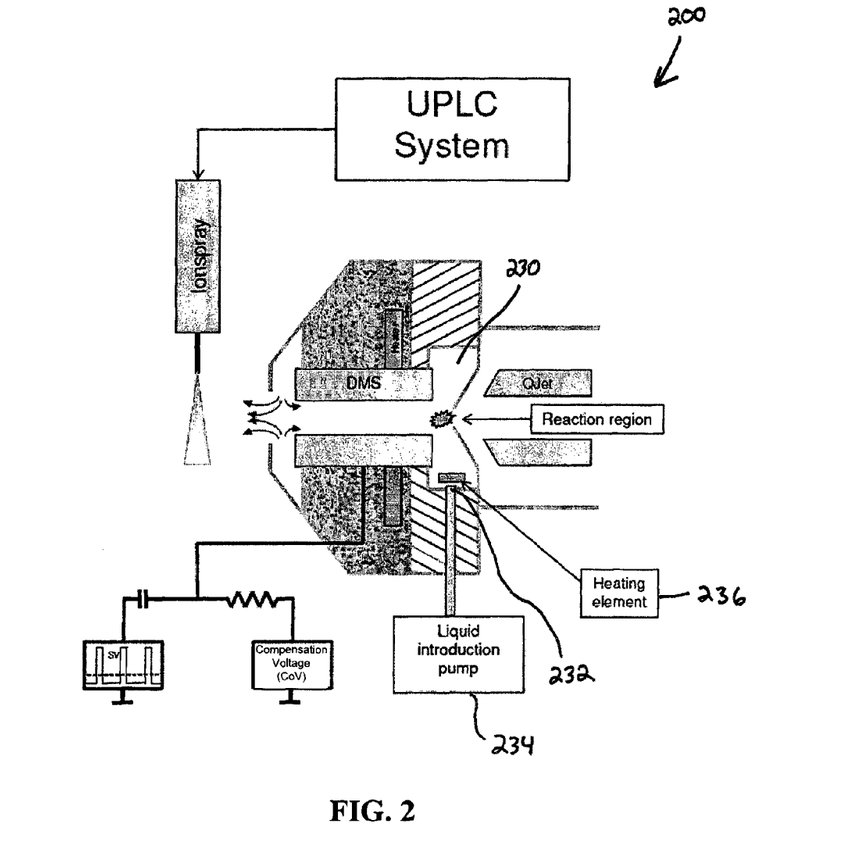
FIG. 2, in a schematic diagram, illustrates another exemplary differential mobility spectrometer system/mass spectrometer system having a reaction chamber for performing ion/molecule reactions in accordance with an aspect of various embodiments of the applicants' teachings.

Moreover, it will be appreciated that a neutral reagent can be introduced into a reaction chamber for reaction with the analyte ions between a differential mobility spectrometer and downstream mass spectrometer elements without the addition of a throttle gas as described above with reference to FIG. 1. For example, with reference now to FIG. 2, there is illustrated in a schematic diagram, a mass spectrometer system 200 in accordance with an aspect of a second embodiment of the present invention. For clarity, elements of the system 200 of FIG. 2 that are analogous to elements of the system 200 of FIG. 1 are designated using the same reference numerals as in FIG. 1, with 100 added. The mass spectrometry system 200 is substantially similar to that depicted in FIG. 1 but differs in that a liquid neutral reagent can be pumped into the reaction chamber 230 via a nozzle 232 in communication with a liquid reagent supply 234. Moreover, a heater 236 can be provided so as to control the desolvation of a liquid solvent droplet produced by the nozzle 232 and containing the neutral reagent. As will be appreciated by a person skilled in the art, a liquid containing the neutral reagent can be metered into the reaction chamber 230, for example, through an LC pump, syringe pump, or other dispensing device for dispensing the neutral reagent into the reaction chamber 230 at a known rate.

Figure 3:
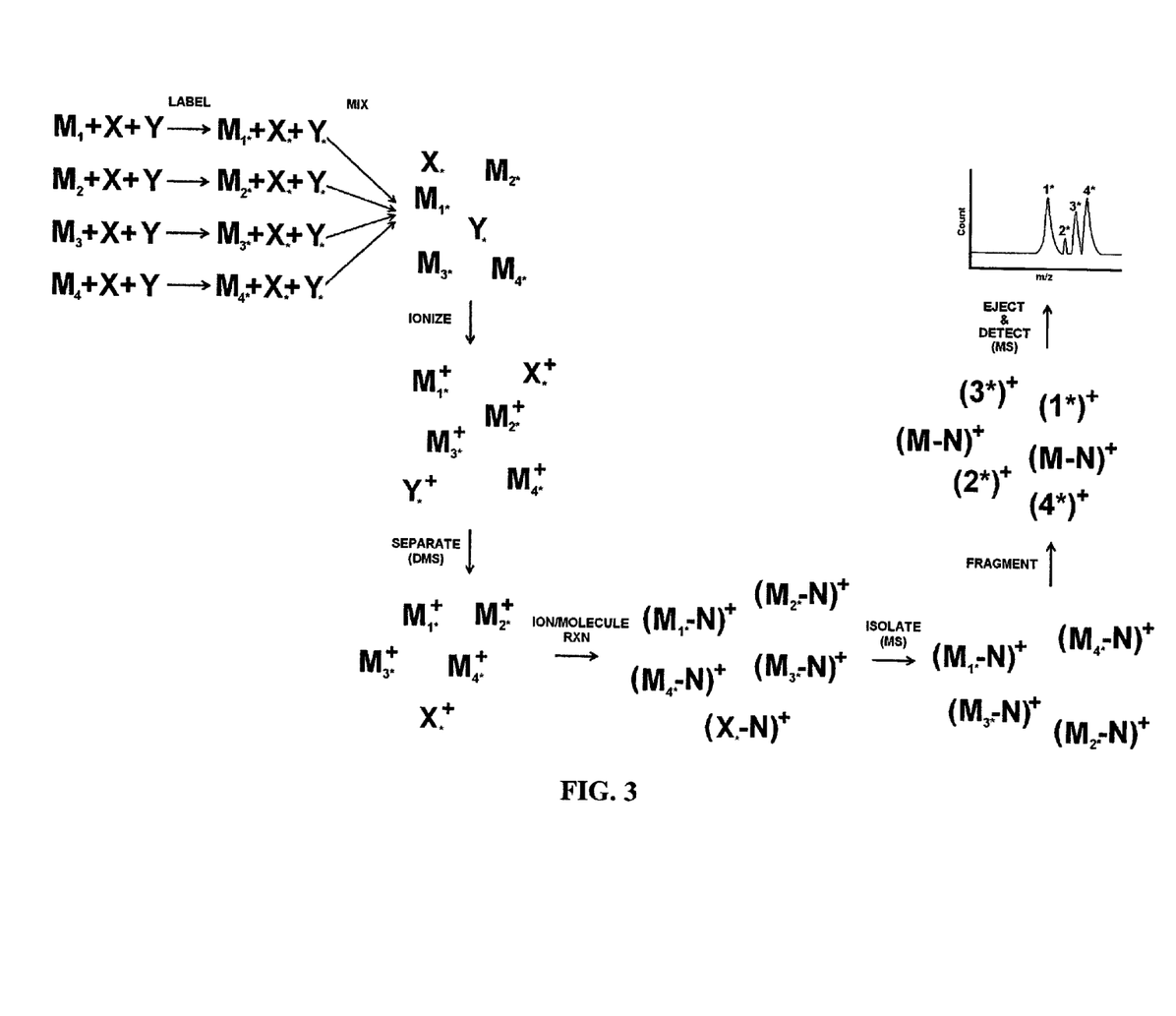
FIG. 3 depicts an exemplary multiplexed mass spectrometric experiment in accordance with aspects of various embodiments of the applicants' teachings.

The applicants' teachings can be even more fully understood with reference to the exemplary experiment presented in FIG. 3, which provides an exemplary method for performing multiplexed quantitative proteomics in accord with various aspects of the applicants' teachings.

In an exemplary operation, two or more samples (e.g., protein digestion, blood, serum, plasma, urine, saliva, etc.) can be obtained, prepared in accordance with standard techniques known in the art, and reacted with an isobaric labeling reagent such as an iTRAQ or TMT labeling reagent such that the various peptides within each sample become associated with a reporter group that expresses a characteristic MS signal. By way of example, with specific reference to the experiment depicted in FIG. 3, four samples (n=4), each of which contains a plurality of peptides ($M_n$+X+Y), can be reacted with an isobaric labeling reagent having a unique reporter group. For ease of description, the analyte of interest from each sample is referred to as $M_n$, with various other species of peptides contained within each sample generally referred to as X and Y. Because of the non-specific reaction of the labeling reagent with the peptides contained in each sample, the peptides $M_n$, X, and Y in each sample can be associated with the unique, isobaric labeling reagent to form $M_n$*, X*, and Y. The various samples can then be mixed (i.e., multiplexed) as is known in the art such that each analyte of interest is subject to identical downstream MS/MS conditions. By way of example, the mixed samples can be prepared for MS analysis, for example, by being run through an UPLC column and subsequently ionized by an ion source. A person skilled in the art will appreciate that though the labeled peptides $M_n$*, X*, and Y* are shown to co-elute, the UPLC can be effective to remove various other analytes that are present in the sample prior to ionization of the labeled analytes ($M_n$*, X*, and Y*). As shown in FIG. 3, ionization of the labeled analytes can be effective to generate labeled analyte ions ($M_n$*+, X*$^{30}$, and Y*+).

In accordance with various aspects of the applicants' teachings, the labeled analyte ions ($M_n^{*+}$, $X^{*+}$, and $Y^{*+}$) can be subjected to an initial mobility-based separation, for example, by being introduced into a differential mobility spectrometer. As will be appreciated by a person skilled in the art, the conditions of the ion mobility separation can be selected so as to transmit through the differential mobility spectrometer only the analyte of interest, and in some cases analytes having similar mobilities under the particular differential mobility spectrometer conditions. By way of example, the SV and CV can be selected based on historical data such that the labeled analyte ions of interest ($M_n^{*+}$) are preferentially transmitted by the differential mobility spectrometer. As shown in FIG. 3, for example, though the differential mobility spectrometer conditions might transmit labeled analyte ions ($X^{*+}$) in addition to the labeled analyte ions of interest ($M_n^{*+}$) (i.e., the $M_n^{*+}$ and $X^{*+}$ ions have similar mobilities in the particular conditions), the differential mobility spectrometer can be effective to remove various other species of labeled analyte ions ($Y^{*+}$) based on differences in mobility. As noted above, the differential mobility spectrometer can also operate in "transparent" mode to pass substantially all of the labeled analyte ions ($M_n^{*+}$, $X^{*+}$, and $Y^{*+}$), or alternatively, the differential mobility spectrometer can be removed from the mass spectrometer system altogether.

As discussed above, though a high-resolution mass analyzers may be able to discriminate between a target species exhibiting a m/z that differs from that of an interfering species by as little as 0.1 Th, mass spectrometric analysis of compounds that have been labeled with isobaric tags is generally performed at lower resolution (e.g., ~1-4 Th). Moreover, as will be appreciated by a person skilled in the art, a target species and an interfering species can exhibit identical m/z ratios.

By way of non-limiting example, though the labeled analyte ions of interest ($M_n^{*+}$) and the labeled analyte ions ($X^{*+}$) present in the ionized, labeled sample can have different masses, each can exhibit ~m/z of 500. For example, the labeled analyte ions of interest ($M_n^{*+}$) can have a molecular mass of 2000 Da at a +4 charge state while the labeled analyte ions ($X^{*+}$) can have a molecular mass of 1500 Da at a +3 charge state. As such, in a standard MS/MS analysis, a low-resolution MS isolation in Q1 would allow both the labeled analyte ions of interest ($M_n^{*+}$) and the labeled interfering analyte ions ($X^{*+}$) to be transmitted for downstream MS analysis. Subsequent fragmentation of the precursor ions and detection of the child reporter ions would not accurately reflect the quantity of the analyte of interest (M) present in a sample and/or the ratio of the quantity of the analyte of interest ($M_n$) present in various multiplexed samples.

In order to effect the separation of the labeled analyte ions of interest ($M_n^{*+}$) and the labeled interfering analyte ions ($X^{*+}$), ion/molecule reactions can be performed to alter one or both of the charge state and/or mass of the labeled analyte ions ($M_n^{*+}$, $X^{*+}$) such that the various species would become resolvable due to difference in their modified m/z. By way of example, as discussed above with reference to FIG. 1, the labeled analyte ions transmitted by the differential mobility spectrometer 120 into the reaction chamber 130 can be subject to ion/molecule reactions with a neutral reagent (N) contained within a throttle gas such that the m/z of the product $[(M_n^*-N)^+]$ of the reaction of the labeled analyte ions of interest ($M_n^{*+}$) with the neutral reagent (N) differs from the m/z of the product $[(X^*-N)^+]$ of the reaction of the labeled interfering ions ($X^{*+}$) with the neutral reagent (N). Examples of suitable ion/molecule reactions include ion-molecule adduct formation, condensation reactions, displacement/elimination reactions, clustering reactions, charge exchange reactions and proton transfer reactions, all by way of non-limiting example. By way of example, with reference to the particular exemplary analyte ions having an identical ~m/z 500 described above (i.e., the target species ion has a molecular mass of 2000 Da at a +4 charge state and the interfering species has a molecular mass of 1500 Da at a +3 charge state), an ion/molecule reaction can be effective to modify the molecule (e.g., reduce the charge state) for each species such that the target species has an ~m/z of 667 (2000 Da at +3 charge state) and the interfering species has an ~m/z of 750 (1500 Da at +2 charge state).

As a result of the difference in the modified m/z, a low-resolution MS isolation can be effective to isolate the target labeled analyte ions $[(M_n^*-N)^+]$ from the interfering analyte ions $[(X^*-N)^+]$, as indicated in FIG. 3. Subsequent fragmentation (e.g., via CID in a collision cell) of the target labeled analyte ions $[(M_n^*-N)^+]$ can cleave the reporter ions $(n^*)^+$ and allow for their subsequent ejection and/or detection, as is known in the art. The exemplary chromatogram depicted in FIG. 3 can be used, for example, to determine the relative or absolute quantities of the analyte of interest $M_n$ present in the four samples.

Other embodiments of the applicants' teachings will be apparent to those skilled in the art from consideration of the present specification and practice of the present teachings disclosed herein. It is intended that these examples be considered as exemplary only.

As such, methods in accord with various aspects of the teachings herein enable improved specificity in discriminating between the analyte of interest and interfering species when using mass spectrometry isobaric tagging techniques. Moreover, in various aspects, the applicants' teachings enable separations based on differential mobility to reduce advantageously the population of ions subject to ion/molecule reactions, reactions which can be difficult to control as the number of ions increases. Further, use of the differential mobility spectrometer to isolate the target analyte ions from interfering ions can advantageously prevent the depletion of the neutral reagent molecules in downstream ion/molecule reactions.

The section headings used herein are for organizational purposes only and are not to be construed as limiting. While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art.

The invention claimed is:

1. A method for performing mass spectrometry, comprising:
   reacting at least one sample with a labeling reagent to generate a plurality of labeled analytes, the sample containing or suspected of containing an analyte of interest;
   ionizing said plurality of labeled analytes to generate a plurality of labeled analyte ions, wherein said plurality of labeled analyte ions comprises labeled ions of the analyte of interest, if any, and labeled ions of an interfering species, the labeled ions of the interfering species being characterized by a m/z ratio substantially identical to that of the labeled ions of the analyte of interest;
   reacting the labeled analyte ions with a neutral reagent to change the charge state of at least one of the labeled ions of the analyte of interest and the labeled ions of the interfering species such that a m/z ratio of the labeled ions of the analyte of interest differs from a m/z ratio of the labeled ions of the interfering species; and, subsequently:

isolating the labeled ions of the analyte of interest from the labeled ions of the interfering species based on said difference in m/z ratio;

fragmenting the labeled ions of the analyte of interest so as to cleave a reporter group therefrom; and detecting the reporter group.

2. The method of claim 1, wherein reacting the at least one sample with a labeling reagent comprises reacting each of two or more samples with a different isobaric labeling reagent, the method further comprising mixing the plurality of labeled analytes from the two or more samples.

3. The method of claim 2, wherein each of the isobaric labeling reagents comprise a reporter group, and wherein the reporter groups of each of the different isobaric labeling reagents differ in mass.

4. The method of claim 3, wherein each of the reporter groups is detected.

5. The method of claim 1, wherein charge states of the labeled ions of the analyte of interest and the labeled ions of the interfering species differ prior to reacting the labeled analyte ions with a neutral reagent.

6. The method of claim 1, wherein the analyte of interest and the interfering species comprise peptides.

7. The method of claim 1, further comprising transporting said labeled analyte ions through an ion mobility spectrometer prior to reacting the labeled analyte ions with the neutral reagent.

8. The method of claim 7, wherein the ion mobility spectrometer comprises a differential mobility spectrometer.

9. The method of claim 1, further comprising reacting the labeled analyte ions with the neutral reagent while transporting said labeled analyte ions through an ion mobility spectrometer.

10. The method of claim 1, further comprising reacting the labeled analyte ions with the neutral reagent prior to transporting said labeled analyte ions through an ion mobility spectrometer.

11. The method of claim 1, further comprising reacting the labeled analyte ions with the neutral reagent subsequent to transporting said labeled analyte ions through an ion mobility spectrometer.

12. A method for performing mass spectrometry, comprising:

reacting a sample with a labeling reagent comprising a reporter group to generate a plurality of labeled analytes, the sample containing or suspected of containing an analyte of interest;

ionizing said plurality of labeled analytes to generate a plurality of labeled analyte ions, wherein said plurality of labeled analyte ions comprises labeled ions of the analyte of interest, if any, at a first charge state characterized by a first m/z ratio;

reacting the labeled ions of the analyte of interest with a neutral reagent so as to change the charge state of the labeled ions of the analyte of interest to a second charge state characterized by a second m/z ratio different from the first m/z ratio; and fragmenting the labeled ions of the analyte of interest characterized by the second m/z ratio so as to cleave the reporter group from the labeled ions of the analyte of interest; and detecting the reporter group.

13. The method of claim 12, wherein the labeled analyte ions are reacted with a neutral reagent at least one of before, during, or after transporting said labeled analyte ions through a differential mobility spectrometer.

14. A mass spectrometry system, comprising:

a differential mobility spectrometer for receiving ions from an ion source, the differential mobility spectrometer having an internal operating pressure, electrodes, and at least one voltage source for providing DC and RF voltages to the electrodes;

a mass spectrometer sealed to, and in fluid communication with, the differential mobility spectrometer for receiving the ions from the differential mobility spectrometer;

a vacuum chamber surrounding the mass spectrometer for maintaining the mass spectrometer at a vacuum pressure lower than the internal operating pressure, such that the vacuum chamber is operable to draw a gas flow including the ions through the differential mobility spectrometer and into the vacuum chamber; and, a reaction chamber connecting an outlet of the differential mobility spectrometer to an inlet of the mass spectrometer to define an ion path of travel therebetween, the reaction chamber configured for reacting ions with a neutral reagent molecule prior to entry in the mass spectrometer.

15. The system of claim 14, wherein the reaction chamber comprises a port for delivering neutral reagent molecules to the reaction chamber.

16. The system of claim 15, wherein the port comprises a nozzle for delivering a liquid neutral reagent.

17. The system of claim 15, wherein the port supplies a gas into the reaction chamber, wherein the gas is configured to be bubbled through a neutral reagent supply prior to introduction in the reaction chamber.

18. The system of claim 17, wherein the gas port is adjustable to vary a concentration of the neutral reagent molecule into the reaction chamber.

19. The system of claim 17, wherein the gas port is adjustable to vary a gas flow rate through the differential mobility spectrometer.

20. The system of claim 15, further comprising a supply of neutral reagent molecules, the supply being connected to the port.

* * * * *